United States Patent [19]

Pellico

[11] Patent Number: 4,626,558

[45] Date of Patent: Dec. 2, 1986

[54] DENTAL IMPRESSION COMPOSITION CONTAINING FINELY SIZED POLYACRYLAMIDE

[75] Inventor: Michael A. Pellico, Los Angeles, Calif.

[73] Assignee: Laclede Professional Products, Inc., Gardena, Calif.

[21] Appl. No.: 785,985

[22] Filed: Oct. 10, 1985

[51] Int. Cl.$^4$ .................................................. A61K 6/10
[52] U.S. Cl. ...................................... 523/109; 524/28; 524/555; 433/214
[58] Field of Search ........................... 523/109; 524/28; 433/214

[56] References Cited

U.S. PATENT DOCUMENTS

| | | | |
|---|---|---|---|
| 4,468,484 | 8/1984 | Pellico | 523/109 |
| 4,515,913 | 5/1985 | Pellico | 523/109 |
| 4,543,372 | 9/1985 | Watanabe | 523/109 |

*Primary Examiner*—C. Warren Ivy
*Attorney, Agent, or Firm*—Donald Diamond

[57] ABSTRACT

Powdered alginate compositions containing polyacrylamide in an amount from about 0.01 to about 0.25 wt. % and having a particle size less than about 300 mesh have enhanced smoothness characteristics, without visible signs of undissolved polymer, upon admixing with water to obtain orally settable, dental impression material.

11 Claims, No Drawings

DENTAL IMPRESSION COMPOSITION CONTAINING FINELY SIZED POLYACRYLAMIDE

BACKGROUND OF INVENTION

This invention relates to dental preparations and, more particularly, to powdered alginate compositions which are adapted to be admixed with water to provide orally settable, dental impression material.

Alginate compositions have long been used in dentistry as impression material for making impressions in areas in which partial dentures are to be constructed, for fabricating study models in orthodontic treatment, for making primary impressions in endentulous mouths, and as corrective materials in secondary impressions of all types.

As distinguished from agar-based thermally reversible hydrocolloids which gel by lowering the temperature of the heated and fluidized material, alginate compositions gel by means of a chemical reaction. After the alginate gel is formed, it cannot be converted to a fluid condition or sol by physical means and, thus, the alginates are known as irreversible hydrocolloids. The use of alginates in dental therapeutics is reviewed in the text entitled *Elements of Dental Materials*, by Ralph Phillips at Chapter 9.

Alginate compositions designed for use in dental therapeutics are typically formulated as powders which are adapted to be mixed with water to form a viscous sol. The sol is carried into the mouth in a perforated impression tray where it forms an elastic gel through a series of chemical reactions. Following formation of the gel, the impression is removed from the mouth for use in the construction of dental forms.

The basic ingredients of an illustrative powdered alginate comprise potassium alginate, calcium sulfate dihydrate, trisodium phosphate and diatomaceous earth, to which there may be added special purpose ingredients such as magnesium oxide and potassium titanium flouride as well as ingredients for color, flavor and preservation.

The significant ingredient in the powdered alginate composition is soluble potassium alginate which is derived from sea kelp. When the powdered alginate composition is mixed with water, the soluble alginate reacts with the calcium sulfate to produce the gel structure of an insoluble calcium alginate. Since this reaction must take place and go to completion in the mouth, it must be delayed until the aqueous composition is placed in the impression tray and carried to the mouth. In order to effect this delay and provide adequate working time, a reaction rate retarder such as trisodium phosphate is incorporated into the composition. The suggested mechanism for the effectiveness of the reaction rate retarder is that the calcium sulfate will react first with the trisodium phosphate before reacting with the soluble alginate and that as long as any trisodium phosphate is present, the gelling reaction between the soluble alginate and the calcium sulfate will be prevented. A filler such as diatomaceous earth is also incorporated into the formulation to increase the strength and stiffness of the gel and to provide a firm surface that is not tacky. The final structure of the gel is characterized as a brush-heap network of fibrils of calcium alginate which holds the excess water, filler and other ingredients.

The following prior art patents illustrate the state of the art with respect to settable alginate compositions:

U.S. Pat. No. 2,657,971 (Lochridge, 1953) discloses the use of tetrasodium salt of ethylene diamine tetra acetic acid as a reaction rate retarder in a powdered alginate composition containing, for example, potassium alginate, calcium sulfate, diatomaceous earth and sodium fluosilicate.

U.K. Pat. No. 936,091 (Lonsdale, 1963) discloses that dimensionally stable impressions can be obtained by the use of sodium flouride and potassium fluorortitanate in a powdered alginate composition containing sodium alginate, calcium sulfate dihydrate, sodium tripolyphosphate, diatomaceous earth and a blend of light and ultra-light magnesium oxide.

U.K. Pat. No. 951,547 (Nordin, 1964) discloses that dimensionally stable impressions can be obtained by the addition of powdered aluminum to a powdered alginate composition containing sodium alginate, calcium sulfate, sodium flouride, zinc oxide, magnesium oxide, sodium tripolyphosphate, and diatomaceous earth as well as lead silicate.

U.S. Pat. No. 3,268,348 (Morrell, 1966) and U.K. Pat. No. 1,159,471 (Morrell, 1969) disclose, respectively, the use of barium fluoride and lithium fluoride in powdered alginate compositions containing potassium alginate, calcium sulphate dihydrate, tetrasodium pyrophosphate, magnesium oxide and diatomaceous earth whereby impressions made therefrom do not require any treatment in an aqueous fixing bath containing an inorganic salt and that models or casts produced from such impressions possess hard smooth surfaces, which are free from chalkiness and dusting in handling during use of the same or in storage.

U.K. Pat. No. 1,365,024 (Marrickville Holdings Ltd., 1974) discloses that dental impression material having improved flexibility and strength can be prepared from powdered alginate compositions containing potassium alginate, tetrasodium, pyrophosphate, sodium silicofluoride, sodium metasilicate, sodium fluoride, zinc fluoride and synthetic calcium sulfate comprising a blend of calcium sulfate hemihydrate and calcium sulfate dihydrate.

U.S. Pat. No. 4,381,947 (Pellico, 1983) discloses an interactable, two-component, paste system for preparing alginate impression material wherein one component contains an alkali metal alginate in an aqueous paste and the other component contains a divalent metal salt such as calcium sulfate and a reaction rate retarder such as tetrasodium pyrophosphate in a fluid plasticizer that is substantially free of unbound water.

U.S. Pat. No. 4,394,172 (Scheuble et al., 1983) discloses the use in powdered alginate compositions of a coating agent such as polypropylene glycol to provide a non-dusting and fast wetting composition.

U.S. Pat. No. 4,468,484 (Pellico, 1984) discloses an interactable, two-component, paste system for preparing alginate impression material wherein one component contains an alkali metal alginate and polyacrylamide in an aqueous paste and the other component contains a divalent metal salt such as calcium sulfate and a reaction rate retarder such as tetrasodium pyrophosphate in a fluid plasticizer that is substantially free of unbound water. The presence of polyacrylamide provides a non-grainy, smooth admixture of the components.

U.S. Pat. No. 4,515,913 (Pellico, 1985) discloses that powdered alginate compositions formulated with a polymer comprising polyacrylamide have enhanced smoothness characteristics upon admixing with water to obtain orally settable, dental impression material. This patent further discloses that the polyacrylamide is generally present in the powdered alginate composition in an amount from about 0.5 to about 6.0 wt. %.

Although the use of polyacrylamides in powdered alginate compostions constitutes a significant advance in the art, it has been discovered that the concentration of polyacrylamide, for enhancing smoothness of the aqueous mixing step, can be substantially reduced by employing finely sized polyacrylamide. A further advantage of the finely sized polyacrylamide is that it more rapidly dissolves in the aqueous mix.

SUMMARY OF THE INVENTION

In accordance with one aspect of this invention, there is provided a powdered alginate composition that contains from about 0.01 to about 0.25 wt. % of polyacrylamide having a particle size which is less than about 300 mesh which provides a smooth admixture of the powdered alginate composition with water in the preparation of an orally settable, dental impression material.

In accordance with a second aspect of this invention, there is provided a method for preparing an orally settable, dental impression material which comprises admixing from about 2.0 to about 3.0 parts by weight of water with about 1.0 part by weight of a powdered alginate composition that contains from about 0.01 to about 0.25 wt. % of polyacrylamide having a particle size which is less than about 300 mesh which improves the smoothness of the admixing step.

DETAILED DESCRIPTION

The polyacrylamides which can be used in this invention have a molecular weight from about 200,000 to about 6,000,000 and, preferably, a molecular weight from about 5,000,000 to about 6,000,000. To achieve the benefits of this invention, the particle size of the polyacrylamide is generally less that about 300 mesh, and preferably, less than about 350 mesh. The lower limit in polyacrylamide particle size is dictated by practical and economic considerations. The term "mesh" means U.S. Standard Sieve Series (1940) corresponding to National Bureau of Standards LC 584. Polyacrylamide is generally present in the powdered alginate composition in an amount from about 0.01 to about 0.25 wt. % and, preferably, from about 0.02 to about 0.1 wt. %.

Polyacrylamides which are well suited for use in this invention include those which are available under the trademark CYANAMER from American Cyanamid Company, Chemical Products Division, Wayne, N.J. 07470 as, for example, CYANAMER p-250 identified as a homopolymer of acrylamide having a molecular weight of approximately 5,000,000 to 6,000,000. However, the specifications for CYANAMER P-250 polyacrylamide disclose that a maximum of 12% is retained on a 20 mesh screen and that a maximum of 30% passes through a 100 mesh screen. Accordingly, CYANAMER P-250 must be subjected to a separation procedure as, for example, a screening separation in order to obtain polyacrylamide having the requisite particle size. Oversize polyacrylamide can be ground in suitable pulverizing equipment to obtain additional polyacrylamide of the desired size.

The powdered alginate compositions, which are improved by adding polyacrylamides thereto, typically contain an alkali metal alginate, calcium sulfate, a phospate, a fluoride, magnesium oxide, color and flavor ingredients, and a filler.

The alkali metal alginates which can be used include sodium alginate, potassium alginate and mixtures thereof. The alginate is generally present in the powdered composition in an amount from about 6 to about 10 wt. % and, preferably, in an amount from about 8 to about 9 wt. %. The calcium sulfate reactant is, preferably, calcium sulfate dihydrate which is known commercially as terra alba. Calcium sulfate dihydrate is generally present in the powdered composition in an amount from about 6 to about 12 wt. % and, preferably, in an amount from about 7 to about 11 wt. %. The reaction rate retarders which can be utilized in the invention include, for example, tetrasodium pyrophosphate, sodium tripolyphosphate and mixtures thereof. The phosphate retarder is generally present in the powdered composition in an amount from about 0.6 to about 1.6 wt. % and, preferably, in an amount from about 0.7 to about 1.2 wt. %. The fluoride constituent of the composition may be an alkali metal flouride but, preferably, is a double metal fluoride salt such as potassium titanium fluoride, potassium zinc fluoride and the like. The fluoride constituent is generally present in the composition in an amount from about 1 to about 3 wt. %, and, preferably, in an amount from about 1.5 to about 2.5 wt. %. The magnesium oxide component may be light magnesium oxide or a mixture of light and heavy magnesium oxide. The magnesium oxide component is generally present in the composition in an amount from about 2 to about 6 wt. % and, preferably, in an amount from about 3 to about 5 wt. %. Color, flavor and preservative ingredients can be present in trace amounts. A filler such as diatomaceous earth is included in the composition in an amount to make up 100 wt. %.

In use, about 1.0 parts by weight of the polyacrylamide modified powdered alginate composition is admixed, by spatulation, with about 2.0 to about 3.0 parts by weight of water and, preferably, with about 2.2 to about 2.8 parts by weight of water to attain a smooth, paste-like, dental impression material. Spatulation of the aqueous mix may take place in about one half to one minute, and it is then transferred to an impression tray which is applied to a dental area in the mouth where an impression is to be taken. The formulation of the orally, settable, dental impression material is so designed that it sets in the mouth in about three and one-half to about four minutes. Upon completion of the impression taking step, the impression material is removed from the mouth and used in the preparation of a "stone" cast or model. A suitable plaster of Paris composition made up to proper consistency with water may be used in making the stone cast or model.

EXAMPLES

The following examples illustrate the benefits that are achieved by using, in powdered alginate compositions, polyacrylamide having a particle size less than about 300 mesh. The powdered alginate compositions set out in the examples were prepared and evaluated by taking 20 grams of the blended mixture and admixing the same, by spatulation, with 50 grams of water for about 30 seconds and observing the aqueous mixing characteristics. The CYANAMER trademark used in the examples identifies the polyacrylamide which has been hereinabove described.

EXAMPLE 1

| INGREDIENTS | PARTS BY WEIGHT | |
|---|---|---|
| | 1(a) | 1(b) |
| Diatomaceous earth | 66.5 | 66.0 |
| Sodium alginate | 11.0 | 11.0 |
| Calcium sulfate dihydrate | 9.0 | 9.0 |
| Magnesium oxide | 4.5 | 4.5 |
| Potassium titanium fluoride | 3.5 | 3.5 |
| Tetrapotassium pyrophosphate | 1.5 | 1.5 |
| Fructose | 3.5 | 3.5 |
| CYANAMER P-250 (150 mesh) | 0.5 | — |
| CYANAMER P-250 (100 mesh) | — | 1.0 |

Example 1(a) was smooth during the mixing step but there were noticeable undissolved particles of CYANAMER P-250. Example 1(b) was smooth during the mixing step but there were more undissolved particles of CYANAMER P-250 than in Example 1(a).

EXAMPLE 2

| INGREDIENTS | PARTS BY WEIGHT | |
|---|---|---|
| | 2(a) | 2(b) |
| Diatomaceous earth | 66.08 | 66.01 |
| Sodium alginate | 11.00 | 11.00 |
| Calcium sulfate dihydrate | 9.00 | 9.00 |
| Magnesium oxide | 4.50 | 4.50 |
| Potassium titanium fluoride | 3.50 | 3.50 |
| Tetrapotassium pyrophosphate | 1.50 | 1.50 |
| Fructose | 3.50 | 3.50 |
| CYANAMER P-250 (350 mesh) | 0.02 | 0.09 |

Example 2(a) was smooth during the mixing step and there were no visible particles of CYANAMER P-250. Example 2(b) was very smooth during the mixing step and there were no visible signs of undissolved CYANAMER p-250.

Thus, by using polyacrylamide have a particle side less than about 300 mesh, smoothness in the aqueous mxing step can be achieved with substantially less polyacrylamide than that called for and described in the prior art.

In view of the foregoing description and examples it will become apparent to those of ordinary skill in the art that equivalent modifications thereof may be made without departing from the spirit and scope of this invention.

That which is claimed:

1. In a powdered alginate, dental impression composition that is adapted to be mixed with water and is orally settable, said powdered alginate composition containing:
    from about 6 to about 10 wt. % of an alkali metal alginate selected from the group consisting of sodium alginate, potassium alginate and mixtures thereof,
    from about 6 to about 12 wt. % of a calcium sulfate reactant,
    from about 0.6 to about 1.6 wt. % of a reaction rate retarder selected from the group consisting of phosphate, pyrophosphate and tripolyphosphate salts of sodium, potassium and mixtures thereof, and
    filler,
    the improvement which comprises polyacrylamide in said powdered alginate composition in an amount from about 0.01 to about 0.25 wt. %, said polyacrylamide having a particle size less than about 300 mesh, to thereby effect a smooth admixture of the powdered alginate composition with water.

2. The powdered alginate composition of claim 1 wherein the polyacrylamide is present in an amount from about 0.02 to about 0.1 wt. %.

3. The powdered alginate composition of claim 1 wherein the molecular weight of the polyacrylamide is from about 200,000 to about 6,000,000.

4. The powdered alginate composition of claim 1 wherein the polyacrylamide is a homopolymer of acrylamide having a molecular weight from about 5,000,000 to about 6,000,000.

5. The powdered alginate composition of claim 1 wherein the polyacrylamide has a particle size less than about 350 mesh.

6. In a method for preparing an orally settable, dental impression material which comprises admixing from about 2.0 to about 3.0 parts by weight of water with about 1.0 part by weight of a powdered alginate composition containing:
    from about 6 to about 10 wt. % of an alkali metal alginate selected from the group consisting of sodium alginate, potassium alginate and mixtures thereof,
    from about 6 to about 12 wt. % of a calcium sulfate reactant,
    from about 0.6 to about 1.2 wt. % of a reaction rate retarder selected from the group consisting of phosphate, pyrophosphate and tripolyphosphate salts of sodium, potassium and mixtures thereof, and
    filler,
    the improvement which comprises incorporating polyacrylamide into said powdered alginate composition in an amount from about 0.01 to about 0.25 wt. %, said polyacrylamide having a particle size less than about 300 mesh, to thereby effect a smooth admixture of the powdered alginate composition with said water.

7. The method of claim 6 wherein from about 2.2 to about 2.8 parts by weight of water is admixed with about 1.0 part by weight of powdered alginate composition.

8. The method of claim 6 wherein the powdered alginate composition contains from about 0.02 to about 0.1 wt. % of polyacrylamide.

9. The method of claim 6 wherein the molecular weight of the polyacrylamide is from about 200,000 to about 6,000,000.

10. The method of claim 6 wherein the polyacrylamide is a homopolymer of acrylamide having a molecular weight from about 5,000,000 to about 6,000,000.

11. The method of claim 6 wherein the polyacrylamide has a particle size less than about 350 mesh.

* * * * *